United States Patent [19]
Bianco et al.

[11] Patent Number: 6,096,301
[45] Date of Patent: Aug. 1, 2000

[54] COMBINED INTERFERON/ANTIESTROGEN THERAPY FOR TREATMENT OF BREAST CANCER

[75] Inventors: Sergio Del Bianco; Gigliola Sica, both of Rome, Italy

[73] Assignee: Industria Farmaceutica Serono SpA, Italy

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/027,853

[22] Filed: Mar. 8, 1993

Related U.S. Application Data

[60] Continuation-in-part of application No. 07/584,782, Sep. 19, 1990, abandoned, which is a division of application No. 07/358,475, May 30, 1989, Pat. No. 5,024,833, which is a continuation of application No. 07/170,106, Mar. 10, 1988, abandoned, which is a continuation of application No. 06/917,405, Oct. 10, 1986, abandoned.

[51] Int. Cl.[7] .................................................. A61K 38/21
[52] U.S. Cl. ..................... 424/85.6; 424/85.4; 424/85.7; 514/648; 514/651; 514/874; 564/324
[58] Field of Search ................................. 424/85.4, 85.7, 424/85.6; 514/648, 651, 874; 564/324

[56] References Cited

U.S. PATENT DOCUMENTS

| | | | |
|---|---|---|---|
| 4,992,271 | 2/1991 | Fernandes et al. | 424/85.2 |
| 4,994,556 | 2/1991 | Mitsuhashi et al. | 424/85.6 X |

OTHER PUBLICATIONS

"Cancer of the Female Breast International Mortality Trends" by W.P.D. Logan, W.H.O. Stat. Rep., vol. 28, p. 232, 1975.
"Effects of Human Interferon Alpha–2 and Gamma on Proliferation Estrogen Receptor Content and Sensitivity to Anti–Estrogens of Cultured Breast Cancer Cells" by Ch. Marth et al., vol. 24, Serono Symposia Publications from Raven Press, 1985.
"Two New Estrogen–Supersensitive Variants of the MCF–7 Human Breast Cancer Cell Line" by C. Natoli et al., Breast Cancer Research and Treatment 3, 23–32 (1983).
Kangas, et al., Additive and Synergistic Antitumor Effects with Toremifene and Interferons, J. Steroid Biochem., 36(3) p. 259–62 (1990).
Dimitrov N. V. et al., Interferon As A Modifier Of Estrogen Receptor, Ann. Clin. Lab. Sci. 14:32–39 (1984).
van den Berg, H. W. et al., *The British Journal of Cancer*, 52 (3) : 248, 1987.
Kangas, L et al., "Additive & synergistic effects of a novel anti–estrogen, toremifene . . . ", Med Biol., 63(4), 1985, p. 187–90 (Medline abstract).
Mitchell, M.S., "Breast cancer treatment—current status", Postgrad. Med., 74(3), 161–5,168–72,174–5, (1983 Sep.) (Medline abstract).
Yuang Chi Chang, et al., J. Interferon Res., vol. 3(3), p. 299–304 (1983). (Embase abstract).
Sherwin, S.A. et al., "Recombinant leukocyte A inteferon . . . ", Ann. Intern. Med., vol. 98(5), 1983, pp. 598–602. (Embase abstract).
The Merck Index, An Encyclopedia of Chemicals, Drugs & Biologicals, Eleventh Edition, 1989, pp. 9473 & 9017.
Porzsolt et al., J. Cancer Res. Clin Oncol., vol. 115, pp. 465–469, 1989.
"Rationale For Combining Tamoxifen And Interferon In The Treatment Of Advanced Breast Cancer" by F. Porzsolt et al., J. Cancer Res. Clin. Oncol. (1989) 115:465–469.
Abstracts of 1985 TNO–ISIR meeting on Interferon System on Oct. 13–18, 1985 Sica et al., "Proliferative Effect of Beta–Interferon (Frone) Alone or Combined with Tamoxifen (TAM) in Breast Cancer Cells".
H. W. van den Berg et al., BR.J. Cancer, 55:255, 1987.
Sica et al., Anticancer Res. 6(3 Part A) (Apr. 1986) p. 396.
"Antiestrogens In The Treatment Of Breast Cancer" by Sewa S. Legha et al., Cancer Treatment Reviews (1976) 3, 205–216.
"Endocrine Factors In Breast Cancer", J.C. Allegra, Reviews on Endocrine–Related Cancer (1984), Suppl. 14, 115.
"Comparative Antiproliferative Activity in Vitro of Natural Interferons α and β for Diploid and Transformed Human Cells" by E.C. Borden et al., Cancer Reseach 42, 4948–4953, Dec. 1982.
"Antiproliferative Effect of Natural Beta Interferon on Fresh Tumor Cells Analyzed in a Clonogenic Assay" by David R. Strayer et al., Journal of Interferon Research, 4:627–633 (1984).
"Administration of Fibroblast Interferon to Patients with Advanced Breast Cancer: Possible Effects on Skin Metastasis and on Hormone Receptors" by P. Pouillart et al. Eur. J. Cancer Clin. Oncol. vol. 18, No. 10, pp. 929–935, 1982.

*Primary Examiner*—Chhaya D. Sayala
*Attorney, Agent, or Firm*—Ostrolenk, Faber, Gerb & Soffen, LLP

[57] ABSTRACT

Proliferation of breast cancer is treated by a combined type I interferon/non-steroidal antiestrogen therapy. Preferably antiestrogen treatment is sequential to treatment with interferon.

14 Claims, 2 Drawing Sheets

COMBINED INTERFERON/ANTIESTROGEN THERAPY FOR TREATMENT OF BREAST CANCER

This is a continuation-in-part of application Ser. No. 07/584,782, filed Sep. 19, 1990, now abandoned, which was a division of application Ser. No. 07/358,475, filed May 30, 1989 and now U.S. Pat. No. 5,024,833, which was a continuation of application Ser. No. 07/170,106, filed Mar. 10, 1988, now abandoned, which was a continuation of application Ser. No. 917,405, filed Oct. 10, 1986 and now abandoned.

FIELD OF THE INVENTION

This invention relates to the field of cancer therapy. More particularly, the invention relates to the treatment of breast cancer by administration of type I interferon in conjunction with an antiestrogen.

A preferred embodiment comprises the sequential administration of type I interferon and antiestrogen.

BACKGROUND OF THE INVENTION

Breast cancer causes the death of a quarter of a million women worldwide each year and is estimated to be the leading cause of death in women aged between 35 to 54, being second only to cardiovascular diseases in women aged over 55 (LOGAN W.P.D.: Cancer of the female breast. International mortality trends. W.H.O. Stat. Rep. 28:232, 1975).

Breast cancer accounts for 27% of all malignancies around the world. Historically, the first to discover the role played by endocrine treatment in breast cancer was BEATSON (1896) who observed that breast cancer in pre-menopausal women undergoes remission after oophorectomy.

This finding, subsequently confirmed by other scientists, supported the evidence that at least some breast tumors are directly dependent on hormones for their growth and created interest in the therapeutic approach of endocrine organ ablation for the purpose of removing the endogenous source of hormones.

As drugs specifically antagonizing the oestrogen action were discovered, they became an attractive alternative to surgical ablation.

Several antiestrogen compounds have been tested in pre- and post-menopausal women in phase I and II clinical trials. So far, Tamoxifen has proved to be the drug best approaching the effectiveness of surgical endocrine therapy and the one that is substantially free from serious side effects.

A comprehensive review of the therapeutic efficacy of antiestrogens in the treatment of breast cancer is LEGHA S. S. and CARTER S. K.: Anti-estrogens in the treatment of breast cancer. Cancer Treat. Rev. 3:205, 1976.

Another review more specifically related to clinical experience with Tamoxifen is that of PATTERSON J. S., et al: A review of the International clinical experience with Tamoxifen. Jpn. J. Cancer clin. 11 (Suppl.): 157, 1981.

Approximately one-third of women with breast cancer respond to antiestrogen-based hormonal therapy, while an increase up to 70% of response is expected in patients with receptor-rich tumors. In fact, estrogen receptor (ER) status has been demonstrated to be predictive of response in breast cancer patients—ALLEGRA J. C.: Reviews on Endocrine related cancer. (Paterson AHG, Lees A W eds) Suppl. 14:115, 1984.

Interferons are a well-known family of proteins which have been shown to possess both antiviral and cell growth inhibitory effects.

Human interferons are grouped into three classes based upon differences in biological and immunological properties as well as molecular structures.

Interferons are also classified, in accordance with their chemical sensitivity to acid pH, into two types:

TYPE I: Acid-stable (alpha from leukocytes, alpha from lymphoblasts, beta from fibroblasts);

TYPE II: Acid-labile (gamma from lymphocytes).

Interferons have a wide range of cellular effects on cancer, as well as on normal cells, including such effects on cell phenotype as antigen expression, cell receptors and so on.

The mechanism by which interferons regulate human cell growth has not been completely elucidated.

In particular, very few data are available concerning the antiproliferative activity of interferons on human mammary neoplastic cells and little is known about the factors determining sensitivity of these cells to the interferon action—BORDEN E. C., et al: Comparative antiproliferative activity in vitro of natural interferons for diploid and transformed human cells. Cancer Res. 42:4948–4953, 1982. —STRAYDER D. R., et al: Antiproliferative effect of natural beta interferon on fresh tumor cells analyzed in a clonogenic assay. J. Interferon Res. 4:627–633, 1984.

Experimental evidence exists that type I IFN modifies the hormone receptor level in breast cancer tissue cells. POUILLART T., et al, in: "Administration of fibroblast interferon to patients with advanced breast cancer: possible effects on skin metastasis and on hormone receptors" (Eur. J. Cancer Clin. Oncol. 18:929–935, 1982) described the effect on human fibroblast interferon administered to patients with metastasised breast cancer and found an increase of the receptors for estrogens and progestogens.

DIMITROV N. V., et al, in: "Interferon as a modifier of estrogen receptor" (Ann. Clin. Lab. Sci. 14:32–39, 1984) demonstrated that human leukocyte interferon increases estrogen receptor activity in a cell homogenate of human breast cancer tissue.

Contradictory experimental evidence is that of MARTH Ch., et al, in: "Effects of human Interferon Alpha-2 and Gamma on proliferation, estrogen receptor content, and sensitivity to anti-estrogens of cultured breast cancer cells" (The Interferon System, Ed. F. Dianzani, G. B. Rossi, Serono Symposia Publs. from Raven Press, Vol. 24, 1985) who were unable to demonstrate any influence by interferon alpha on estrogen receptor content in cultured breast cancer cells. The conclusion thus reached by the authors is that estrogen action is independent of interferon since the growth inhibition by anti-estrogens is not affected by interferon treatment.

DETAILED DESCRIPTION OF THE INVENTION

Figure 1A:
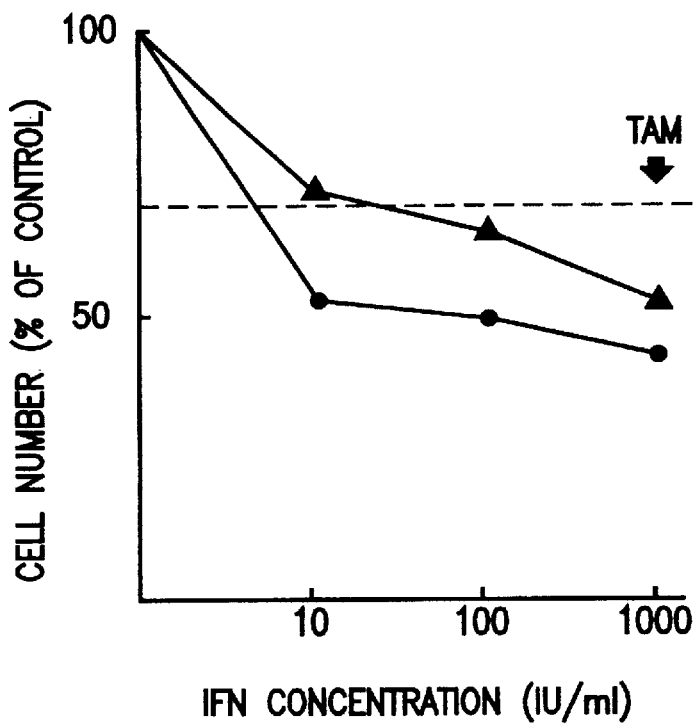
FIGS. 1a and 1b demonstrate the effect of interferon and tamoxifen added simultaneously (large dot symbol) or sequentially (triangular symbol) to CG-5 cells on the third (a) and sixth (b) day from the addition of the compounds to the culture medium.

In accordance with the present invention, the combined treatment with type I interferon and anti-estrogen has been shown to be highly effective in treating the proliferation of the growth of breast cancer cells. Particularly good results are obtained when the administration of the antiestrogen is sequential to a treatment with type I interferon.

It is therefore an object of this invention to provide a method of treating of breast cancer by administering type I interferon in conjunction with an anti-estrogen.

A further object of this invention is to provide a method of treating the proliferation of breast cancer by the sequential administration of type I interferon and anti-estrogen.

Within the meaning of "type I interferon" both alpha and beta human interferons are included. The interferons can be either "native", that is obtained from natural human sources or cell lines, or "recombinant", that is obtained from genetically engineered or otherwise modified bacterial, yeast or eukaryotic cells.

Although tamoxifen is the preferred antiestrogen, other substances having analogous activity are within the meaning of "antiestrogen" in accordance with the present invention. Suitable examples are found, e.g., in the above mentioned review by Legha and Carter where such antiestrogens are further characterized as being non-steroidal.

The finding on which this invention is based is that the new combined treatment of breast cancer cells gives results that could not be predicted from the known antiproliferative effect of interferon or the demonstrated efficacy of an antiestrogen when used separately.

Preliminary in vitro experiments were carried out on CG-5 cells, a variant of the MCF-7 cell line characterized by a high degree of estrogen responsiveness and an appreciable content of estrogen, androgen, glucocorticoid and progesterone receptors—Natoli C. et al: Two new estrogen supersensitive variants of the MCF-7 human breast cancer cell line—(Breast Cancer Res. Treat. 3, 23–32, 1983).

Cells were routinely cultured in Dulbecco's modified Eagle's medium (DMEM) supplemented with 10% fetal calf serum (FCS) and antibiotics.

For cell growth experiments cells were plated out at the density of 50,000 cells/ml in the medium described above. 24 hours later, the medium was replaced with fresh medium containing 5% charcoal-treated FCS (CH-FCS) plus a fixed concentration ($10^{-7}M$) of tamoxifen (TAM) and various concentrations (from 10 to 1000 IU/ml) of interferon beta (IFN). Medium was renewed every 3 days.

In the experiments concerning the effects of IFN and TAM sequentially added to CG-5 cells, cells were plated out at 50,000 cells/ml, as described above, and 24 hours later DMEM was changed with fresh medium containing 10 to 1000 IU/ml of IFN. For each concentration of IFN a different number of plates were prepared in order to have, at the end of the treatment, a sufficient number of cells to be replaced (as IFN has an inhibitory effect itself). After 1 week of exposure to IFN, CG-5 cells were plated in medium supplemented with 10% FCS and antibiotics, and 24 hours later DMEM was replaced by fresh medium supplemented with 5% CH-FCS and a fixed concentration of TAM ($10^{-7}M$). Medium was renewed every 3 days.

In all the experiments performed cells were counted, after 3 to 6 days, with the use of an hemocytometer.

The addition to CG-5 cultures of a fixed concentration of TAM ($10^{-7}M$), combined to concentrations ranging from 10 to 1000 IU/ml of IFN, produces an inhibition of cell proliferation which is not related to the dose of IFN, but is higher than that induced by TAM alone, even at the lowest concentration of IFN (about 50% with respect to control) on the third day from the addition of the two drugs to the culture medium.

When cells are treated for 6 days with the combined TAM-IFN, the inhibition of cell proliferation becomes dependent on the dose of IFN and reaches 65% with respect to controls at 1000 IU/ml of the drug.

If CG-5 cells are pretreated with different concentrations of IFN and subsequently exposed to $10^{-7}M$ TAM, 3 days after the addition of the antiestrogen to the culture medium, a relevant inhibition of cell proliferation is seen (approximately 50% with respect to control) in the cells which received the highest concentration of IFN.

On the sixth day after the addition of TAM to the culture medium, the most pronounced inhibition of cell proliferation is obtained in CG-5 cells pretreated with the lowest concentration of IFN (about 65% with respect to control) and it remains unmodified in cells pretreated with increasing doses of the drug.

Figure 1B:
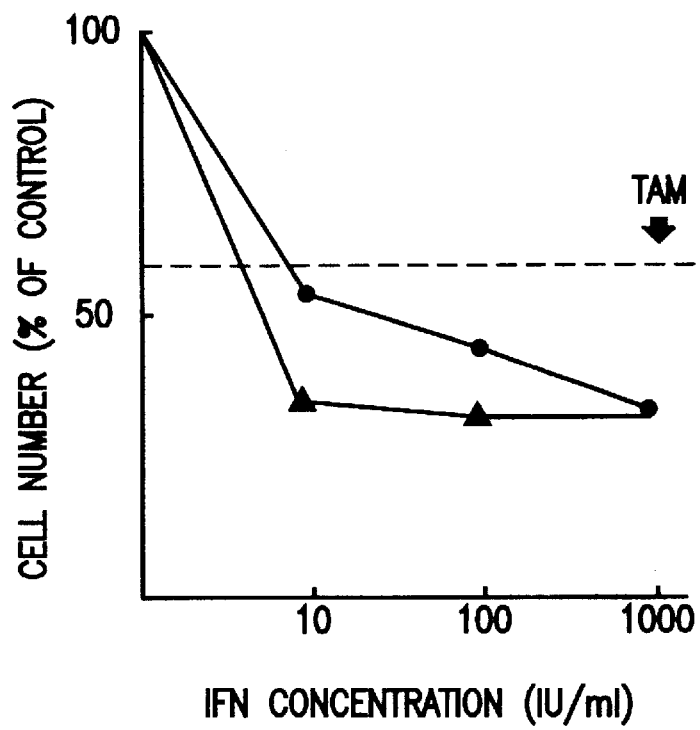

Results are summarized in FIG. 1, a and b, which illustrate graphically the comparison between the different modalities (combined or sequential treatment) used to study the effect of tamoxifen and interferon on cell growth.

Graphs a and b demonstrate the effect of interferon and tamoxifen added simultaneously (large dot symbol) or sequentially (triangular symbol) to CG-5 cells on the third (a) and sixth (b) day from the addition of the compounds to the culture medium. In the case of sequential administration cells were pretreated with the interferon concentration indicated in the figure and then exposed to tamoxifen. The dotted line (---) represents the effect of $10^{-7}M$ tamoxifen alone, evaluated in parallel experiments not reported in the text.

Figure 2:
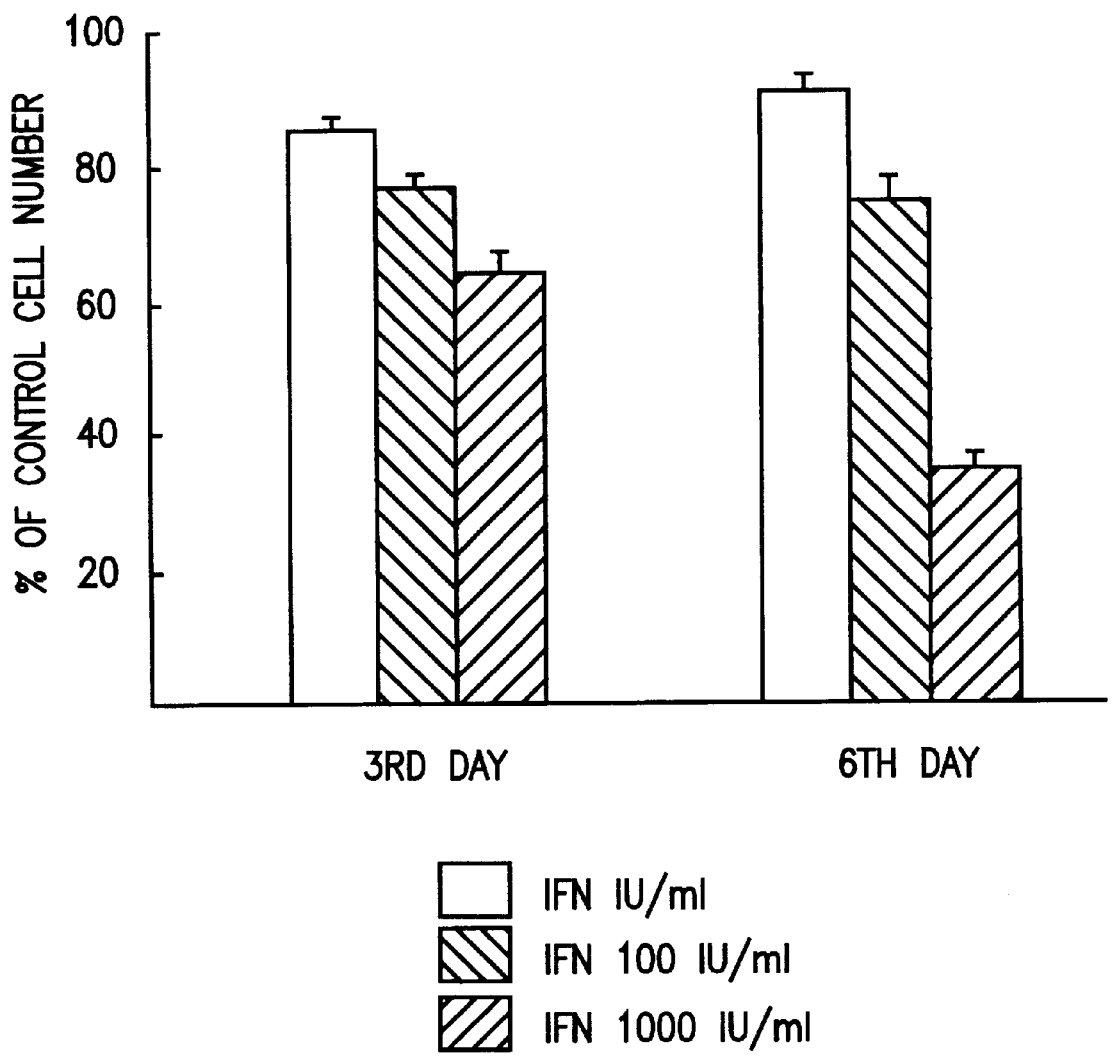
FIG. 2 shows the effect of interferon alone on the growth of CG-5 cells.

FIG. 2 shows the effect of interferon alone on the growth of CG-5 cells cultured in identical experimental conditions. In this case the inhibition of cell proliferation is evident after three days of exposure to the interferon from the concentration of 100 IU/ml. After six days of treatment with interferon, the inhibitory effect on cell proliferation significantly increases only at the maximum dose of 1000 IU/ml.

The comparison between FIGS. 1 and 2 clearly shows that such low doses of interferon as 10 IU/ml result is efficacious when combined with the anti-estrogen, whereas the same doses are practically ineffective if interferon is used alone.

Similar conclusions are reached if the effect of tamoxifen alone is compared with the combined effect of tamoxifen with interferon.

The efficacy of the combined therapy according to this invention is established by clinical trials conducted in patients responding to the following criteria:

Patients with superficial biopsiable, histologically confirmed advanced breast cancer;
Patients in postmenopausa;
ER/PR status: positive or unknown (provided at least 2 years of disease free interval);
No concurrent radiotherapy or chemotherapy;
No brain metastases.

Each patient receives intramuscular injections of interferon doses ranging from 2 to 10 million International Units and is given orally a fixed dose of the antiestrogen corresponding to the dose known to be optimal for breast cancer treatment. For example, in the case of tamoxifen, the most suitable daily dose is 30 milligrams.

When interferon alpha is used, injected doses are generally higher than the doses of interferon beta.

Examples of suitable treatment schedules are as follows:
1) Interferon administered three times a week for two to four weeks;
Antiestrogen administered daily for 8 weeks starting immediately after discontinuation of interferon administration.

2. Interferon administered three times a week for two to four weeks;

Antiestrogen administered daily for 12 weeks starting on the same day the interferon treatment starts.

3. Interferon administered daily for one to four weeks;

Antiestrogen administered daily for 12 weeks starting the day after the last interferon administration.

4. The same treatment scheduled (3) above with once a week additional administration of interferon in the period of antiestrogen therapy.

The main criterion of evaluation is the evidence of response documented on the basis of tumor regression by measurement of palpable lesions and changes in X-Ray or computerized tomography scan or ultrasonic echography appearances.

The increase of estrogen receptors in the patients is also taken into consideration as a laboratory datum supplementing clinically assessed responsiveness.

The efficacy of the combined interferon/antiestrogen treatment in the proliferation of breast cancer is thus established.

Various changes and modifications can be made in the therapeutic method of the present invention without departing from the spirit and scope thereof. The embodiments described herein are for the purpose of illustrating the invention but are not intended to limit it.

What is claimed is:

1. In a method of treating breast cancer cells in a human patient by administering a non-steroidal antiestrogen thereto, the improvement which comprises administering to said patient 10 to 100 IU/ml of interferon beta sequentially prior to the antiestrogen treatment for at least 6 days, wherein said antiestrogen is tamoxifen.

2. The method of claim 1 wherein the interferon beta is administered intramuscularly in an amount of 2 to 10 million International Units per day.

3. The method of claim 1 in which the interferon beta administration period is 1 to 4 weeks.

4. The method of claim 3 in which the antiestrogen administration period is 8 to 12 weeks.

5. The method of claim 4 in which the interferon beta is administered three times per week for 2 to 4 weeks.

6. The method of claim 5 in which the antiestrogen is administered daily.

7. The method of claim 4 in which the interferon beta and antiestrogen are administered daily.

8. The method of claim 4 in which interferon beta is additionally administered periodically during the antiestrogen treatment.

9. The method of claim 8 in which the interferon beta is administered intramuscularly.

10. The method of claim 9 in which the antiestrogen is administered orally.

11. The method of claim 1 in which the antiestrogen is administered intramuscularly.

12. The method of claim 11 in which the antiestrogen is administered orally.

13. The method of claim 1, wherein 10 IU/mg is administered for six days.

14. The method of claim 1, wherein 100 IU/mg is administered for six days.

* * * * *